(12) United States Patent
Koshimizu et al.

(10) Patent No.: US 9,442,056 B2
(45) Date of Patent: Sep. 13, 2016

(54) HARDNESS TESTER

(71) Applicant: MITUTOYO CORPORATION, Kanagawa (JP)

(72) Inventors: Fumihiko Koshimizu, Zama (JP); Takeshi Sawa, Kawasaki (JP)

(73) Assignee: MITUTOYO CORPORATION, Kanagawa (JP)

( * ) Notice: Subject to any disclaimer, the term of this patent is extended or adjusted under 35 U.S.C. 154(b) by 255 days.

(21) Appl. No.: 14/140,046

(22) Filed: Dec. 24, 2013

(65) Prior Publication Data

US 2014/0182364 A1    Jul. 3, 2014

(30) Foreign Application Priority Data

Dec. 28, 2012 (JP) .................................. 2012-286480

(51) Int. Cl.
*G01N 3/42* (2006.01)

(52) U.S. Cl.
CPC ......... *G01N 3/42* (2013.01); *G01N 2203/0033* (2013.01)

(58) Field of Classification Search
CPC ....................................................... G01N 3/42
USPC .......................................... 73/78, 81, 82, 83
See application file for complete search history.

(56) References Cited

U.S. PATENT DOCUMENTS

| | | | | |
|---|---|---|---|---|
| 2,892,344 A * | 6/1959 | Sklar | ......................... | G01N 3/44 279/102 |
| 5,177,999 A * | 1/1993 | Tobolski | .................. | G02B 7/16 73/82 |
| 2010/0313638 A1* | 12/2010 | Handschuck | ............ | G01N 3/42 73/81 |
| 2012/0210777 A1* | 8/2012 | Holl | ......................... | G01N 3/42 73/81 |

FOREIGN PATENT DOCUMENTS

| | | | | |
|---|---|---|---|---|
| JP | 2006-226883 | | 8/2006 | |
| JP | 2006226883 A | * | 8/2006 | ............... G01N 3/42 |

* cited by examiner

*Primary Examiner* — John Fitzgerald
*Assistant Examiner* — Jean Morello
(74) *Attorney, Agent, or Firm* — Greenblum & Bernstein, P.L.C.

(57) ABSTRACT

The hardness tester includes a plurality of weights; a transmission mechanism transmitting to an indenter a force of gravity acting on the weights; and a test force switching mechanism switching between magnitudes of a test force. The weights include hollow portions running through the weights in a vertical direction; and accommodation portions formed so as to be capable of accommodating the weight directly below. Outside tapered portions are provided to an exterior surface of the weights and inside tapered portions are provided to an interior surface of the accommodation portions. The transmission mechanism includes a shaft member and a weight engagement portion capable of being accommodated by the bottom-most accommodation portion to engage a weight. The weight engagement portion includes a tapered portion engaging the weight to regulate horizontal-direction displacement. A predetermined gap is reserved between the hollow portions and the shaft member.

5 Claims, 12 Drawing Sheets

US 9,442,056 B2

HARDNESS TESTER

CROSS-REFERENCE TO RELATED APPLICATIONS

The present application claims priority under 35 U.S.C. §119 of Japanese Application No. 2012-286480, filed on Dec. 28, 2012, the disclosure of which is expressly incorporated by reference herein in its entirety.

BACKGROUND OF THE INVENTION

1. Field of the Invention

The present invention relates to a hardness tester.

2. Description of Related Art

Conventionally, a hardness tester (such as a Vickers hardness tester, a Rockwell hardness tester, and the like) is known which measures hardness of a sample by applying a test force to a surface of the sample using an indenter having a planar rhomboid shape or an indenter having a conical or spherical tip to form a polygonal indentation. For example, in a case of a lever-type hardness tester, a weight is used to apply the test force to the surface of the sample.

Specifically, as shown in FIG. 10, in a conventional hardness tester 101, a load lever 102 rotates due to a force of gravity acting on a weight 103 and a predetermined load is applied to an indenter column 104a having an indenter 104 at a forefront end thereof. Then, the load applied to the indenter column 104a is transmitted to the indenter 104 to become a test force for forming the indentation in a sample S placed on a sample stage 105. The weight 103 of the hardness tester 101 has a plurality of weights 1031, 1032, and 1033 stacked on top of each other in a vertical direction and also has a shaft member (or shaft) 161 running through a hollow portion of each of the weights 1031, 1032, and 1033. Therefore, the weight 103 of the hardness tester 101 has a shape long in the vertical direction.

In addition, as shown in FIG. 11, a hardness tester 201 is also known in which a shape of a weight 203 is more compact in the vertical direction as compared to the weight 103 of the hardness tester 101 (see, e.g., Japanese Patent Laid-open Publication No. 2006-226883).

However, the indenter is a component formed by an expensive material such as diamond and, in order to prevent damaging accidents and the like due to contact with the sample, a large distance must be kept between a tip of the indenter and the sample during standby for a test. When a large distance is kept between the tip of the indenter and the sample, a distance to the sample when performing the test becomes large, and thus the indenter column must have a greater stroke. Because the indenter column is subject to an action of the load lever, when the stroke of the indenter column is made larger, a rotation amount of the load lever naturally increases. In the conventional case of the hardness tester 101 shown in FIG. 10, for example, in order to apply a load to the indenter 104 with various test forces by combining only the weight 1031, or the weights 1031 and 1032, or the weights 1031, 1032, and 1033, a size of a gap P1 between the weights 1031, 1032, and 1033 must be at least an action stroke or more of the weight 103 due to rotation of the load lever 102. Therefore, when the stroke of the indenter column 104a is increased, the action stroke of the weight 103 due to the rotation of the load lever 102 is increased by an amount of leverage and the size of the gap P1 is further amplified by a number of layers of the weights 103. For example, in a case where the leverage is multiplied by ten and the weights 103 have ten layers, when attempting to amplify the stroke of the indenter column 104a by 1 mm, a space of 1 mm×10 (multiplier)×(10−1) (layers)=90 mm must be reserved. Therefore, there is a problem that the entire tester cannot be made compact.

In addition, in the conventional case of the hardness tester 201 shown in FIG. 11, the weight 203 can be made compact in the vertical direction. However, there is a problem that a horizontal-direction position of the weight 203 cannot be made stable. Specifically, as shown in FIG. 12, weights 2031, 2032, and 2033 each have a margin of horizontal-direction shifting the size of a horizontal-direction gap P2 between each of the weights 2031, 2032, and 2033. In a case where repeated hardness tests are conducted, for example, shifting of the horizontal-direction position of each of the weights 2031, 2032, and 2033 may occur with respect to a shaft member 261, which serves as a positioning reference, and there may be interference between the weights being used for the load and the unused weights. Therefore, there is a risk that a correct test force may be impossible to generate.

SUMMARY OF THE INVENTION

The present invention has as a feature to provide a hardness tester capable of generating an accurate test force while achieving compactness for the entire hardness tester.

An aspect of the invention was made in order to achieve the above-noted object and is a hardness tester measuring hardness of a sample by forming an indentation in a surface of a sample by applying a predetermined test force with an indenter, then measuring dimensions of the indentation. The hardness tester includes a plurality of weights applying the predetermined test force to the sample through the indenter; a transmission mechanism transmitting to the indenter, as the test force, a force of gravity acting on the plurality of weights; and a test force switcher switching a magnitude of the test force by switching between the weights applying the test force. The plurality of weights are stacked on top of each other in a vertical direction. The plurality of weights include hollow portions running through a horizontal-direction center in the vertical direction; and accommodation portions formed so as to be capable of accommodating the weight located directly below. An exterior surface of the weights is provided with an outside tapered portion. An interior surface of the accommodation portion is provided with an inside tapered portion engaging with the outside tapered portion of the accommodated weight to regulate horizontal-direction displacement of the weight. The transmission mechanism includes a shaft member running through the hollow portions; and a weight engagement portion provided to a bottom end of the shaft member and capable of being accommodated by the accommodation portion of the bottom-most weight to engage the weight. The weight engagement portion includes a tapered portion for engagement engaging with the inside tapered portion of the bottom-most weight to regulate the horizontal-direction displacement of the bottom-most weight. A predetermined gap is reserved between the hollow portions and the shaft member.

Another aspect of the invention is the hardness tester, wherein the plurality of weights is formed so as to have a truncated cone shape in a state where the plurality of weights are stacked on top of each other.

Another aspect of the invention is the hardness tester, wherein the test force switcher includes a cam member positioned so as to be below the plurality of weights and so as to be capable of rotation concentric with the plurality of weights, and formed such that a horizontal-direction width changes according to a rotation angle; and a weight support supporting the weights and formed by a pair of members positioned so as to be mutually point-symmetrical in the horizontal direction with the cam member therebetween and a first end being rotatable around a vertical axis. The weight support is continuously biased such that a second end closes toward the cam member and a distance between the second ends changes due to rotating the first ends, caused by rotation of the cam member, thereby switching between which of the plurality of weights is to be supported.

Another aspect of the invention is the hardness tester, wherein the test force switcher includes a notch positioned so as to be capable of supporting bottom ends of the plurality of weights and formed so as to widen toward an open end. In addition, the test force switcher is configured to be capable of advancing and retreating in a direction in which the open end of the notch is formed. Switching between which of the plurality of weights is to be supported is performed by advancing and retreating the test force switcher in the direction in which the open end of the notch is formed.

According to the present invention, a plurality of weights can be stacked on top of each other in a vertical direction while being accommodated in accommodation portions. Therefore, the weights can be made more compact in the vertical direction and an entire tester can be made more compact. Further, inside tapered portions and outside tapered portions are provided to the plurality of weights, and a tapered portion for engagement is provided to a weight engagement portion. Therefore, horizontal-direction displacement of the plurality of weights can be regulated and horizontal-direction shifting of a position of the plurality of weights can be prevented. Thus, an accurate test force can be generated.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

Figure 1:
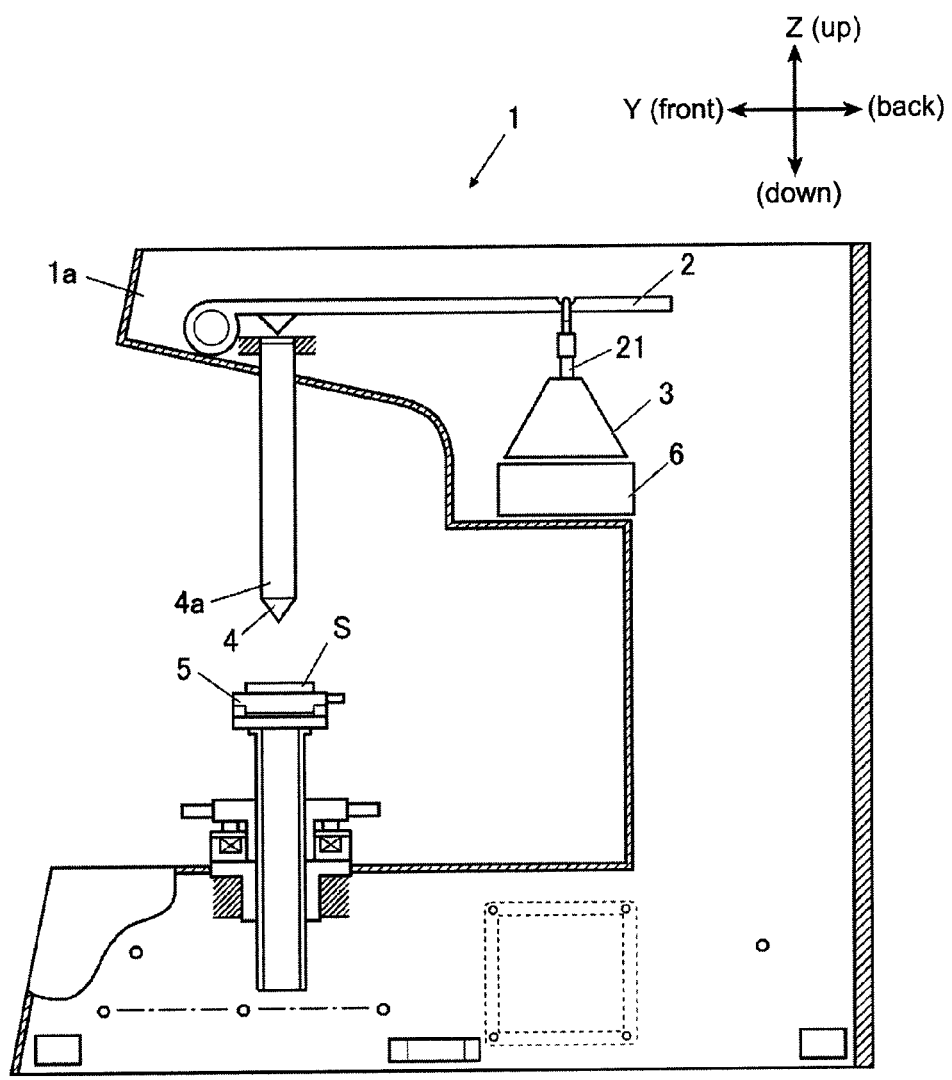
FIG. 1 is a right lateral view illustrating an overall configuration of a hardness tester according to the present invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, an embodiment of the present invention is described in detail with reference to the drawings. Moreover, in the following description, an X direction is a left-right direction, a Y direction is a front-back direction, and a Z direction is an up-down direction in the drawings. In addition, an X-Y plane is a horizontal plane.

A hardness tester 1 is, for example, a Vickers hardness tester having planar surfaces of an indenter 4 forming a square shape. As shown in FIGS. 1 to 7, the hardness tester 1 is configured to include a load lever 2 as a transmission mechanism; a weight 3; the indenter 4 provided to a forefront end of an indenter column 4a; a sample stage 5; and a test force switching mechanism 6 as a test force switcher.

A forward end of the load lever 2 is rotatably supported by a tester main body 1a of the hardness tester 1. At a rear end of the load lever 2, the weight 3 is suspended via a shaft member 21. The weight 3 displaces in a down direction due to gravity, thereby rotating the load lever 2 clockwise in the down direction. In addition, accompanying this rotation of the load lever 2 in the down direction, a predetermined load acts on the indenter column 4a, displacing the indenter column 4a in the down direction.

The weight 3 has a plurality (four in the present embodiment) of weights 31, 32, 33, and 34 stacked on top of each other in a vertical direction, and can thus apply a predetermined test force to the sample S through the indenter 4. In addition, the weight 3 is configured such that the test force switching mechanism 6 can switch between the weights 31, 32, 33, and 34, which apply the test force.

Figure 2:
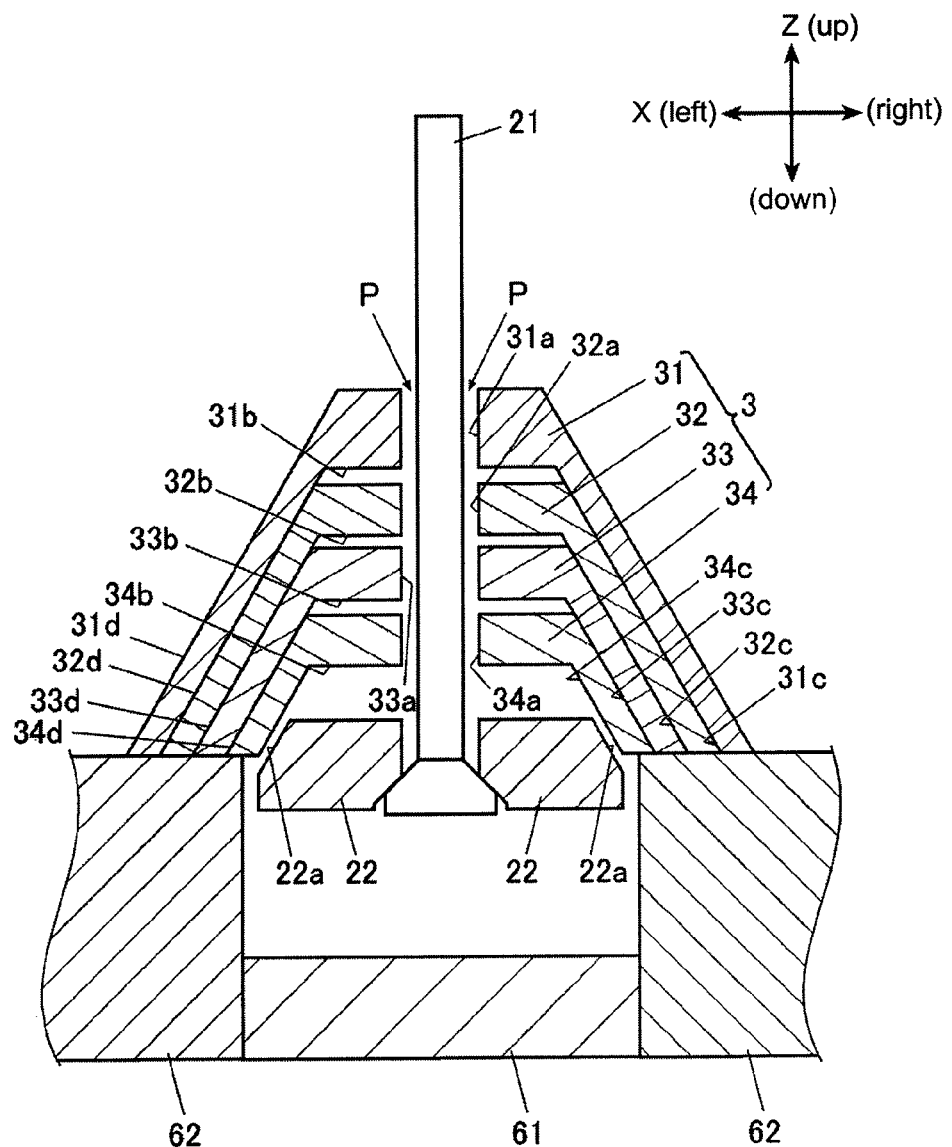
FIG. 2 is a cross-sectional view illustrating a configuration of a weight and a test force switching mechanism in an initial state.

As shown in FIG. 2, the weight 3 has the weights 31, 32, 33 and 34 stacked on top of each other in the vertical direction in order of lightness, each of the weights 31, 32, 33, and 34 having a different predetermined weight. The weight 3 is formed so as to have substantially a truncated cone shape in a state where each of the weights 31, 32, 33, and 34 are stacked on top of each other. A hollow portion 31a, 32a, 33a, and 34a is provided to each of the weights 31, 32, 33, and 34, respectively, the hollow portions 31a, 32a, 33a, and 34a running through a horizontal-direction center in the vertical direction. The shaft member 21 passes through the hollow portions 31a, 32a, 33a, and 34a. The hollow portions 31a, 32a, 33a, and 34a are formed to be wider than the shaft member 21, such that a gap P is formed between the hollow portions 31a, 32a, 33a, and 34a and the shaft member 21. Further, the weights 31, 32, 33, and 34 have, on bottom surfaces of each, accommodation portions 31*b*, 32*b*, 33*b*, and 34*b*, which are formed in substantially a recessed shape capable of accommodating the weight located directly below. Accordingly, the accommodation portion 31*b* can accommodate the weight 32, which is directly below the weight 31; the accommodation portion 32*b* can accommodate the weight 33, which is directly below the weight 32; and the accommodation portion 33*b* can accommodate the weight 34, which is directly below the weight 33. In addition, inside tapered portions 31*c*, 32*c*, 33*c*, and 34*c* are formed on interior surfaces of each of the accommodation portions 31*b*, 32*b*, 33*b*, and 34*b*. Outside tapered portions 31*d*, 32*d*, 33*d*, and 34*d* are formed on exterior surfaces of each of the weights 31, 32, 33, and 34. The inside tapered portions 31*c*, 32*c*, and 33*c* engage with the outside tapered portions 32*d*, 33*d*, and 34*d* of the weights 32, 33, and 34 accommodated in the accommodation portions 31*b*, 32*b*, and 33*b* to regulate horizontal-direction displacement of the weights 32, 33, and 34. Also, the accommodation portion 34*b* on the bottom-most weight 34 can accommodate a weight engagement portion 22 provided to a bottom end of the shaft member 21. A tapered portion 22*a* is formed on the weight engagement portion 22, the tapered portion 22*a* engaging with the inside tapered portion 34*c* of the bottom-most weight 34 to regulate horizontal-direction displacement of the bottom-most weight 34. Thereby, each of the weights 31, 32, 33, and 34 can be stacked on top of each other in the vertical direction via the shaft member 21. Specifically, the load lever 2, the shaft member 21, and the weight engagement portion 22 are a transmission mechanism transmitting to the indenter 4, as the test force, a force of gravity acting on the plurality of weights 31, 32, 33, and 34.

Moreover, the weight 3 displaces in conjunction with the load lever 2 when displacing in the down direction due to the force of gravity, and thus the weight 3 displaces in the down direction so as to trace an arc. Thus, a concern arises that each of the weights 31, 32, 33, and 34 may shift in the horizontal direction by an amount of the gap P formed between the hollow portions 31*a*, 32*a*, 33*a*, and 34*a* and the shaft member 21. However, the inside tapered portions 31*c*, 32*c*, 33*c*, and 34*c*, the outside tapered portions 31*d*, 32*d*, 33*d*, and 34*d*, and the tapered portion 22*a* are provided in the present embodiment, and the horizontal-direction displacement of the weights 31, 32, 33, and 34 is regulated. Therefore, horizontal-direction shifting of a position of the weights 31, 32, 33, and 34 can be prevented.

The indenter 4 provided to the forefront end of the indenter column 4*a* is displaced toward a sample S placed on the sample stage 5 provided below the indenter 4 and presses against the sample S with the predetermined test force. The indenter 4 is displaced accompanying displacement of the indenter column 4*a* in an axially downward direction due to rotation of the load lever 2. Due to the indenter 4 pressing against the sample S with the predetermined test force, an indentation is formed in a surface of the sample S. Moreover, in the present embodiment, a quadrangular pyramidal Vickers indenter (with opposing angles of) 136±0.5° is used as the indenter 4. The sample S is placed on an upper surface of the sample stage 5 and is fixed in place with a sample holder (not shown in the drawings).

Figure 3:
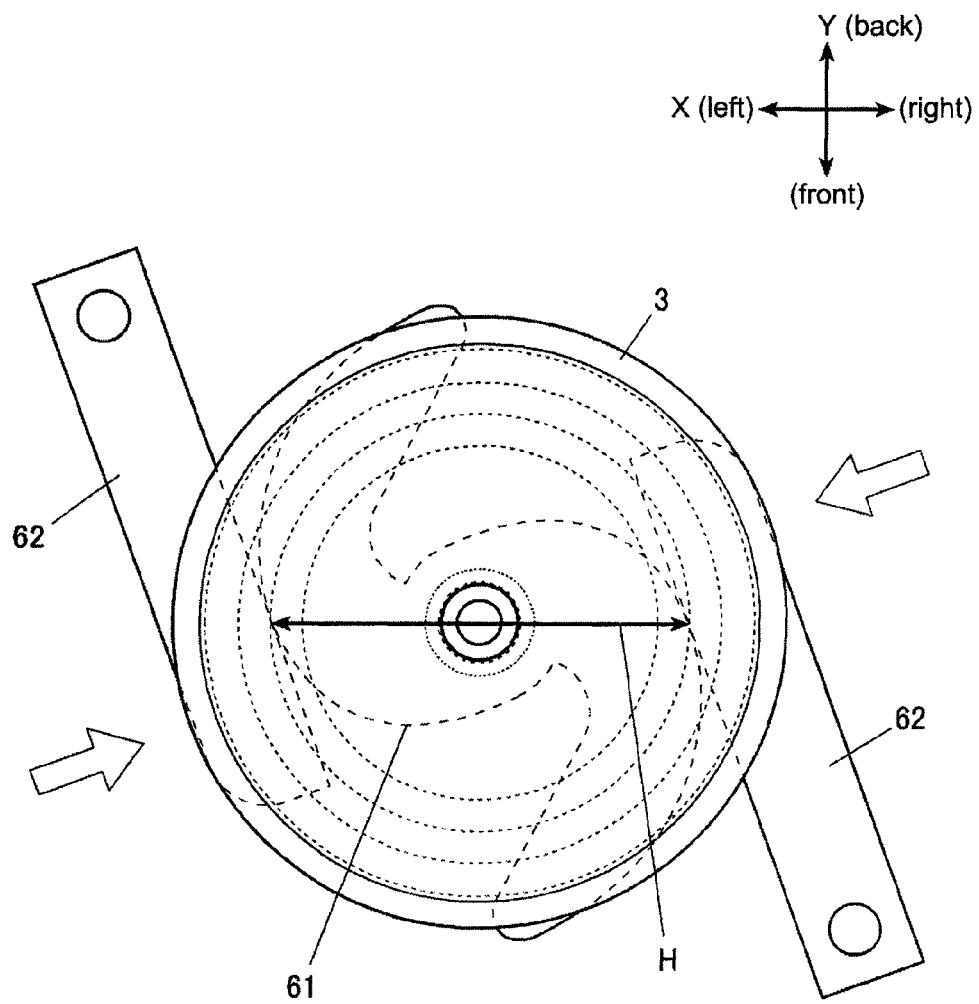
FIG. 3 is a plan view illustrating a configuration of the test force switching mechanism in the initial state.

As shown in FIGS. 2 to 7, the test force switching mechanism 6 is configured to include a cam member 61 and a weight support 62. The cam member 61 is formed in an "S" shape as seen in a plan view, is positioned so as to be below the plurality of weights 31, 32, 33, and 34 and so as to be capable of rotation concentric with the plurality of weights 31, 32, 33, and 34. The cam member 61 is configured so as to freely rotate in the horizontal direction centered on a rotation axis 61*a* provided at a center of the "S," the cam member 61 being rotated by a driver such as a motor (not shown in the drawings). The cam member 61 is formed such that a horizontal-direction (left-right-direction) width H changes according to a rotation angle. Specifically, as shown in FIGS. 2 and 3, the left-right-direction width H of the cam member 61 becomes narrowest in an initial state. Also, as shown in FIGS. 4 to 7, the left-right-direction width H of the cam member 61 gradually increases accompanying rotation. The left-right-direction width H is greatest in a state rotated 90° from the initial state (see FIGS. 6 and 7).

The weight support 62 has a pair of substantially squared columnar members positioned so as to be mutually point-symmetrical in the horizontal direction with the cam member 61 therebetween. A first end of the weight support 62 is formed by a pair of members rotatable around a rotation axis 62*a*, which is a vertical axis. The weight support 62 is continuously biased by an elastic member (e.g., a spring) such that a second end closes toward the cam member 61. Thereby, the weight support 62 continuously abuts and grips the cam member 61. In addition, the weight support 62 is spread outward to counteract a biasing force closing toward the cam member 61 accompanying the left-right-direction width H of the cam member 61 increasing due to rotation of the cam member 61. In other words, a distance between the second ends of the weight support 62 changes due to the first ends of the weight support 62 rotating, caused by rotation of the cam member 61. Further, vertical-direction displacement of the weight support 62 is regulated, so the weight 3 can be supported resting on a top surface of the weight support 62 (see FIGS. 2, 4, and 6). In addition, the weight support 62 is spread outward accompanying rotation of the cam member 61. Thus, a number of weights 3 resting on top of the weight support 62 can be adjusted to select the load (see FIGS. 2 to 7). Specifically, the distance between the second ends of the weight support 62 changes, thus switching between which of the plurality of weights 31, 32, 33, and 34 is to be supported. In other words, the test force switching mechanism 6 can switch the test force by switching between the weights 31, 32, 33, and 34, which apply the test force.

Figure 4:
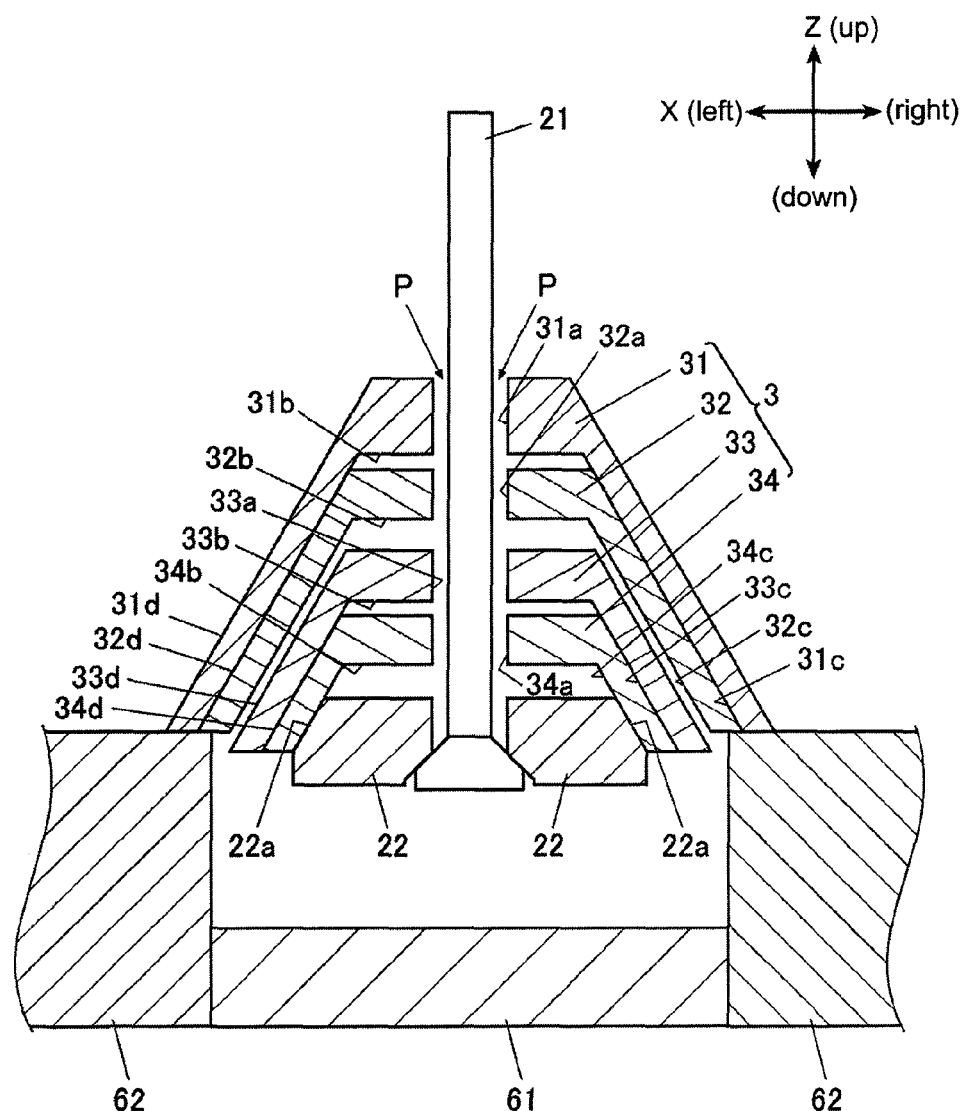
FIG. 4 is a cross-sectional view illustrating a configuration of the weight and the test force switching mechanism after rotating a cam member to a predetermined angle (less than 90°)
Figure 5:
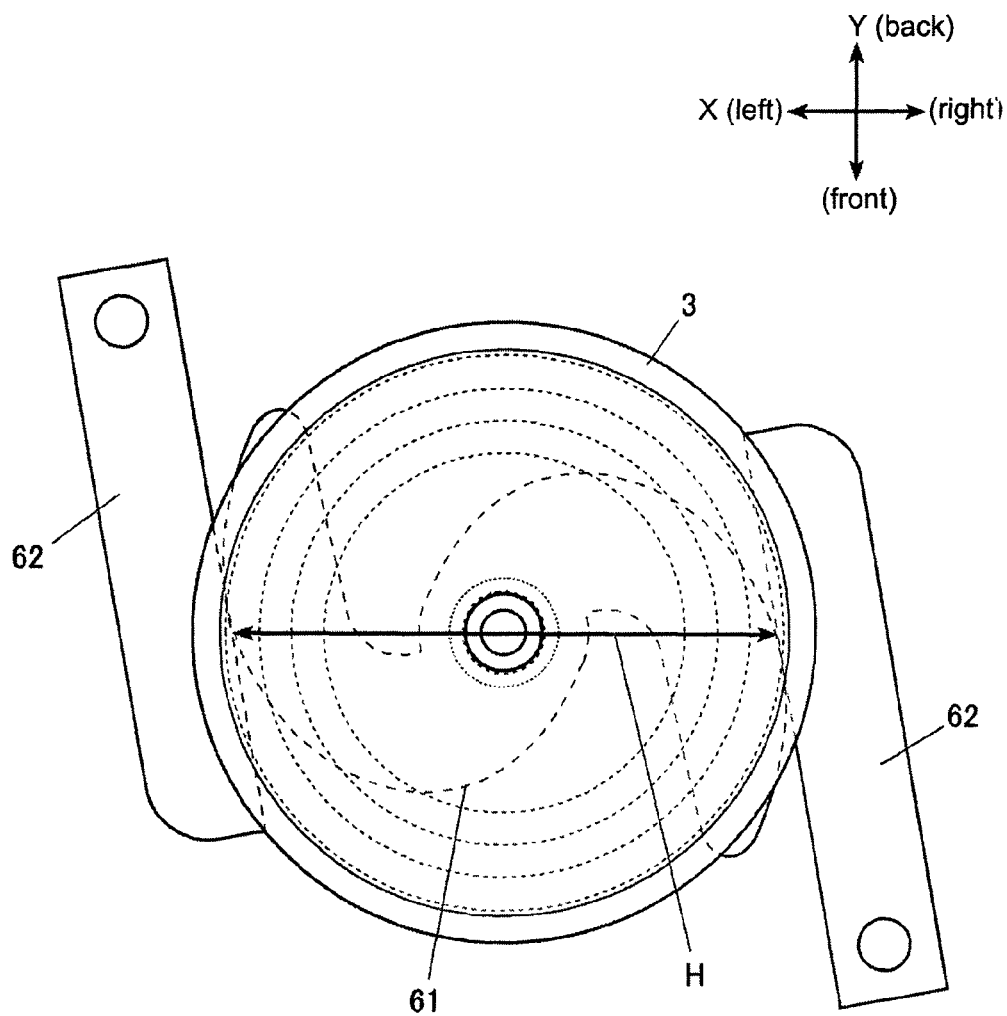
FIG. 5 is a plan view illustrating a configuration of the test force switching mechanism after rotating the cam member to a predetermined angle (less than 90°)
Figure 6:
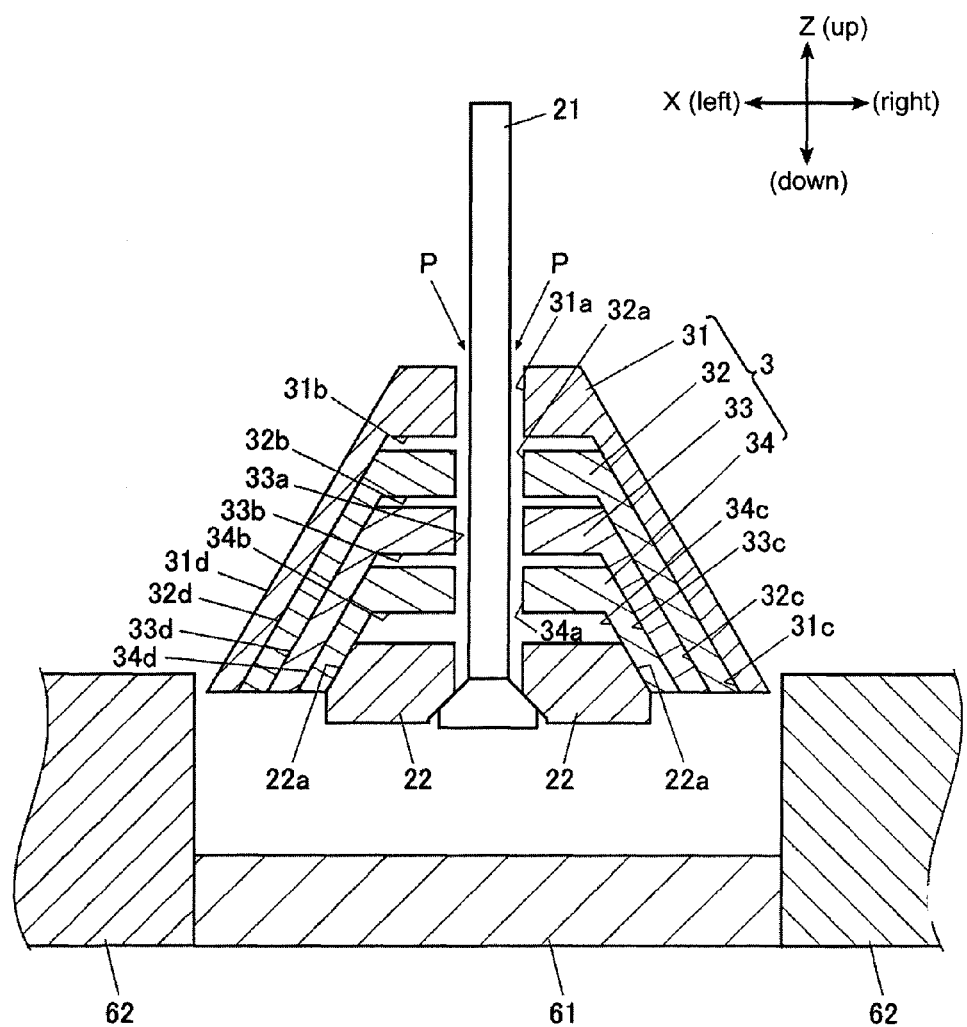
FIG. 6 is a cross-sectional view illustrating a configuration of the weight and the test force switching mechanism after rotating the cam member 90°.
Figure 7:
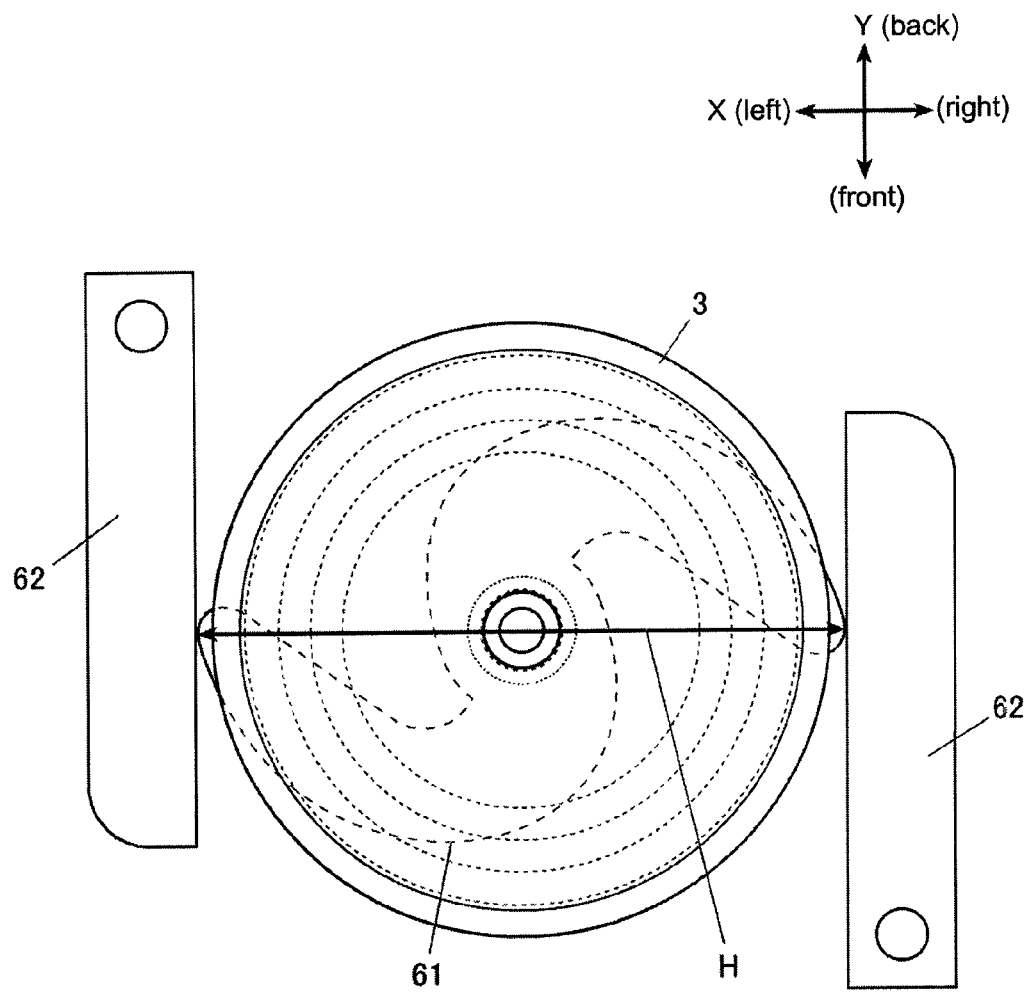
FIG. 7 is a plan view illustrating a configuration of the test force switching mechanism after rotating the cam member 90°.

Next, with reference to FIGS. 2 to 7, a method of switching the test force using the test force switching mechanism 6 is described for the hardness tester 1 according to the present embodiment. In the initial state illustrated in FIGS. 2 and 3, the weights 31, 32, 33, and 34 are all resting on top of the weight support 62. Therefore, no load is acting on the weight engagement portion 22. Accordingly, the initial state is a state in which there is no load in the down direction acting on the load lever 2. In this state, a user rotates the cam member 61 by a predetermined angle and adjusts a position of the weight support 62. For example, as shown in FIGS. 4 and 5, when the weight support 62 is displaced to a position where the weights 31 and 32 are resting thereon, a load corresponding to the weights 33 and 34 is applied to the weight engagement portion 22. Accordingly, in the example shown in FIGS. 4 and 5, a load in the down direction corresponding to the weights 33 and 34 is applied to the load lever 2. Moreover, although omitted from the drawings, when the position of the weight support 62 is adjusted to a position where only the weight 31 is resting thereon, a load in the down direction corresponding to the weights 32, 33, and 34 is applied to the load lever 2, and when adjusted to a position where the weights 31, 32, and 33 are resting thereon, a load in the down direction corresponding to the weight 34 is applied to the load lever 2. Also, as shown in FIGS. 6 and 7, for example, when the cam member 61 is rotated 90° from the initial state and the weight support 62 are displaced to a position where none of the weights 31, 32, 33, and 34 are resting thereon, a load corresponding to all of the weights 31, 32, 33, and 34 is applied to the weight engagement portion 22. Thus, in the example shown in FIGS. 6 and 7, a load in the down direction corresponding to all of the weights 31, 32, 33, and 34 is applied to the load lever 2. As noted above, the user rotates the cam member 61 as appropriate and adjusts the position of the weight support 62. Thus, a number of the weights 3 resting on top of the weight support 62 can be adjusted to select the load applied to the load lever 2.

As noted above, the hardness tester 1 according to the present embodiment includes the plurality of weights 31, 32, 33, and 34 applying the predetermined test force to the sample S through the indenter 4; the transmission mechanism (the load lever 2, shaft member 21, and weight engagement portion 22) transmitting to the indenter 4, as the test force, the force of gravity acting on the plurality of weights 31, 32, 33, and 34; and the test force switching mechanism 6 switching a magnitude of the test force by switching between the weights 31, 32, 33, and 34, which apply the test force. In addition, the plurality of weights 31, 32, 33, and 34 are stacked on top of each other in the vertical direction and each respectively includes the hollow portions 31*a*, 32*a*, 33*a*, and 34*a* running through the horizontal-direction center in the vertical direction; and the accommodation portions 31*b*, 32*b*, 33*b*, and 34*b* formed so as to be capable of accommodating the weight located directly below. Further, the outside tapered portions 31*d*, 32*d*, 33*d*, and 34*d* are provided on the exterior surfaces of the weights 31, 32, 33, and 34 and the inside tapered portions 31*c*, 32*c*, 33*c*, and 34*c* are provided on the interior surfaces of the accommodation portions 31*b*, 32*b*, 33*b*, and 34*b*, the inside tapered portions 31*c*, 32*c*, 33*c*, and 34*c* engaging with the outside tapered portions 32*d*, 33*d*, and 34*d* of the accommodated weights 32, 33, and 34 to regulate the horizontal-direction displacement of the weights 32, 33, and 34. Also, the transmission mechanism includes the shaft member 21 running through the hollow portions 31*a*, 32*a*, 33*a*, and 34*a*; and the weight engagement portion 22 provided to the bottom end of the shaft member 21 and capable of being accommodated by the accommodation portion 34*b* of the bottom-most weight 34 to engage the weight 34. Further, the weight engagement portion 22 includes the tapered portion 22*a* engaging the inside tapered portions 34*c* of the bottom-most weight 34 to regulate the horizontal-direction displacement of the bottom-most weight 34. In addition, the predetermined gap P is reserved between the hollow portions 31*a*, 32*a*, 33*a*, and 34*a* and the shaft member 21. Thus, according to the hardness tester 1 according to the present embodiment, the plurality of weights 31, 32, 33, and 34 can be stacked on top of each other in the vertical direction while being accommodated in the accommodation portions 31*b*, 32*b*, 33*b*, and 34*b*. Therefore, the weight 3 can be made more compact in the vertical direction and the entire tester can be made more compact. Further, the inside tapered portions 31*c* 32*c*, 33*c*, and 34*c* and the outside tapered portions 31*d*, 32*d*, 33*d*, and 34*d* are provided to the plurality of weights 31, 32, 33, and 34, and the tapered portion 22*a* is provided to the weight engagement portion 22. Therefore, the horizontal-direction displacement of the plurality of weights 31, 32, 33, and 34 can be regulated and the horizontal-direction shifting of the position of the plurality of weights 31, 32, 33, and 34 can be prevented. Thus, an accurate test force can be generated.

In addition, according to the hardness tester 1 according to the present embodiment, the plurality of weights 31, 32, 33, and 34 are formed so as to have a truncated cone shape in a state stacked on top of each other in the vertical direction. Therefore, horizontal-direction gaps between the plurality of weights 31, 32, 33, and 34 can be eliminated, thus enabling the horizontal-direction shifting of the position of the plurality of weights 31, 32, 33, and 34 to be more reliably prevented and enabling a more accurate test force to be generated.

In addition, in the hardness tester 1 according to the present embodiment, the test force switching mechanism 6 includes the cam member 61 and the weight support 62. The cam member 61 is positioned so as to be below the plurality of weights 31, 32, 33, and 34 and so as to be capable of rotation concentric with the plurality of weights 31, 32, 33, and 34, and is formed such that the horizontal-direction width thereof changes according to the rotation angle. The weight support 62 supports the weights 31, 32, 33, and 34 and is formed by the pair of members positioned so as to be mutually point-symmetrical in the horizontal direction with the cam member 61 therebetween, the first end being rotatable around the rotation axis 62*a*. Also, the weight support 62 is continuously biased such that the second end thereof closes toward the cam member 61. The distance between the second ends changes due to rotating the first ends, caused by rotation of the cam member 61, thus switching between which of the plurality of weights 31, 32, 33, and 34 is to be supported. Thus, according to the hardness tester 1 according to the present embodiment, the test force switching mechanism 6 is achieved in a simple configuration of the cam member 61 and the weight support 62. Therefore, a number of components can be reduced and costs can be reduced. In addition, by utilizing the cam member 61 formed in the "S" shape, switching of the test force by rotating a maximum of 90° can be achieved, and an amount of rotation (degrees of rotation) of the cam member 61 can be readily recognized.

Above, a concrete description was given based on embodiments according to the present invention. However, the present invention is not limited to the above-described embodiments and may be modified within a scope not deviating from the substance of the invention.

Alternate Example 1

Figure 8:
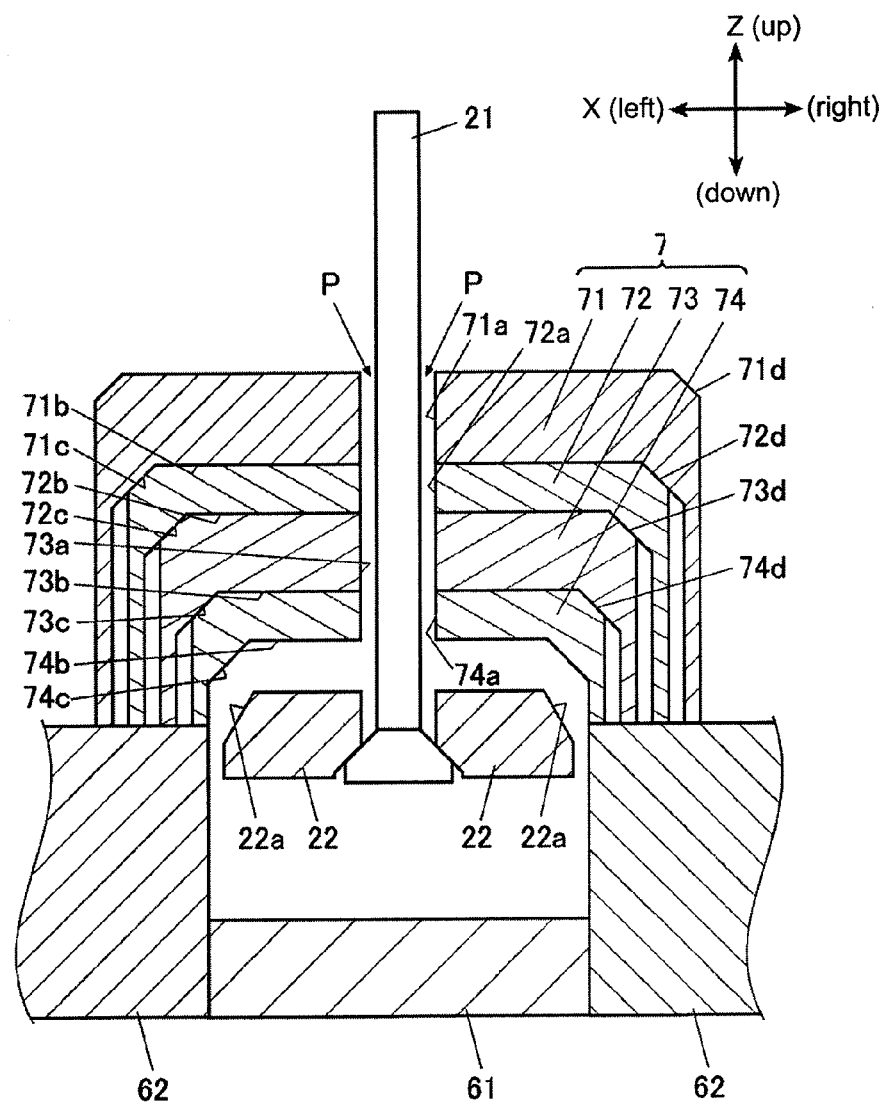
FIG. 8 is a cross-sectional view illustrating an alternate example of a weight.

An example shown in FIG. 8, for example, differs from the embodiment in the shape of the weight 3. In order to simplify the description, identical reference numerals are used for structures similar to those in the embodiment and a detailed description thereof is omitted. Specifically, in the example shown in FIG. 8, a weight 7 has a plurality (three in the present example) of weights 71, 72, and 73 stacked on top of each other in the vertical direction, each of the weights 71, 72, and 73 having a different predetermined weight. The weight 7 is formed so as to have substantially a round columnar shape in a state where each of the weights 71, 72, and 73 are stacked on top of each other. A hollow portion 71*a*, 72*a*, and 73*a* is provided to each of the weights 71, 72, and 73, respectively, the hollow portions 71*a*, 72*a*, and 73*a* running through a horizontal-direction center in the vertical direction. The hollow portions 71*a*, 72*a*, and 73*a* are formed to be wider than the shaft member 21, such that the gap P is formed between the hollow portions 71*a*, 72*a*, and 73*a* and the shaft member 21. Further, the weights 71, 72 and 73 have, on bottom surfaces of each, accommodation portions 71*b*, 72*b*, and 73*b*, which are formed in substantially a recessed shape capable of accommodating the weight located directly below. Accordingly, the accommodation portion 71b can accommodate the weight 72, which is directly below the weight 71, and the accommodation portion 72b can accommodate the weight 73, which is directly below the weight 72. Also, the accommodation portion 73b can accommodate the weight engagement portion 22. In addition, inside tapered portions 71c, 72c, and 73c are formed on interior surfaces of each of the accommodation portions 71b, 72b, and 73b. Outside tapered portions 71d, 72d, and 73d are formed on exterior surfaces of each of the weights 71, 72, and 73. The inside tapered portion 73c of the bottom-most weight 73 is engaged on the tapered portion 22a of the weight engagement portion 22. Thereby, each of the weights 71, 72, and 73 can be stacked on top of each other in the vertical direction via the shaft member 21. The inside tapered portions 71c, 72c, and 73c, the outside tapered portions 71d, 72d, and 73d, and the tapered portion 22a are provided in the present alternate example 1, and the horizontal-direction displacement of the weights 71, 72, and 73 is regulated. Therefore, the horizontal-direction shifting of a position of the weights 71, 72, and 73 can be prevented. In addition, similar to the embodiment, the weight 7 is configured such that the test force switching mechanism 6 can switch between the weights 71, 72, and 73, which apply the test force.

Alternate Example 2

Figure 9A:
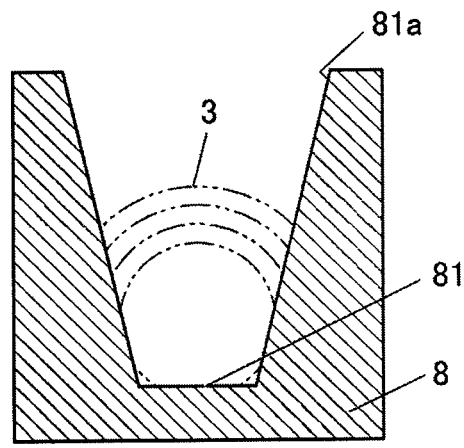
FIGS. 9(A) to 9(C) are bottom views illustrating an alternate example of a test force switching mechanism.
Figure 9B:
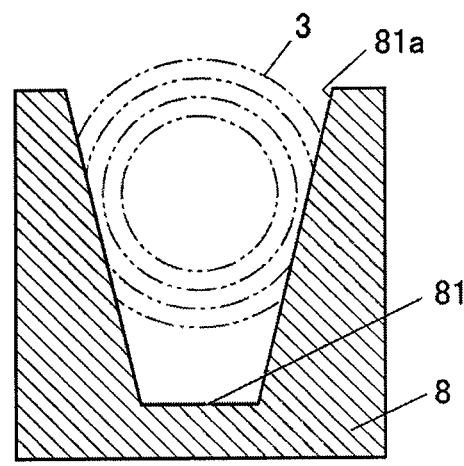
Figure 9C:
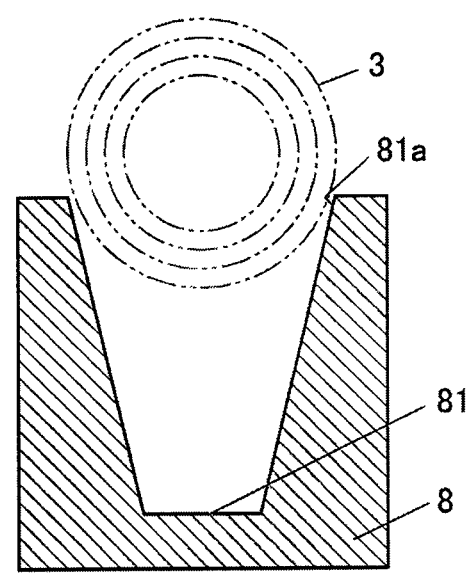
Figure 10:
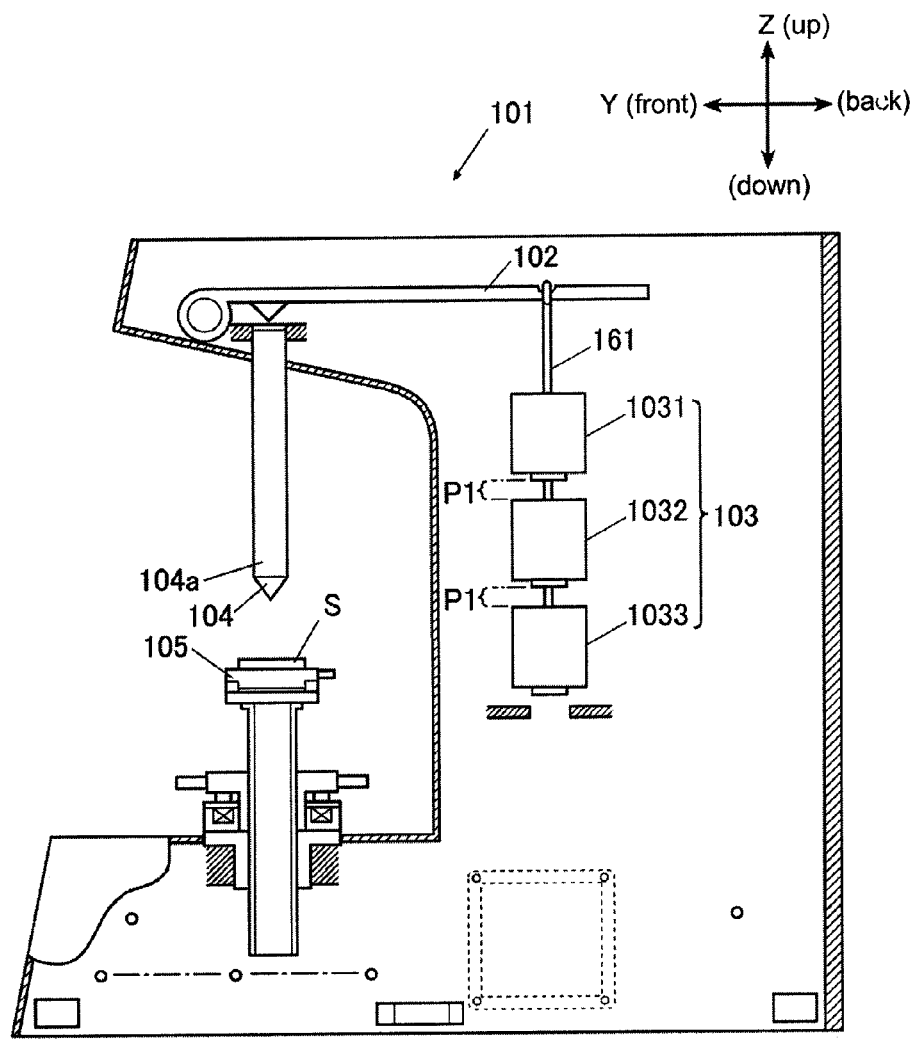
FIG. 10 is a right lateral view illustrating an overall configuration of a conventional hardness tester.
Figure 11:
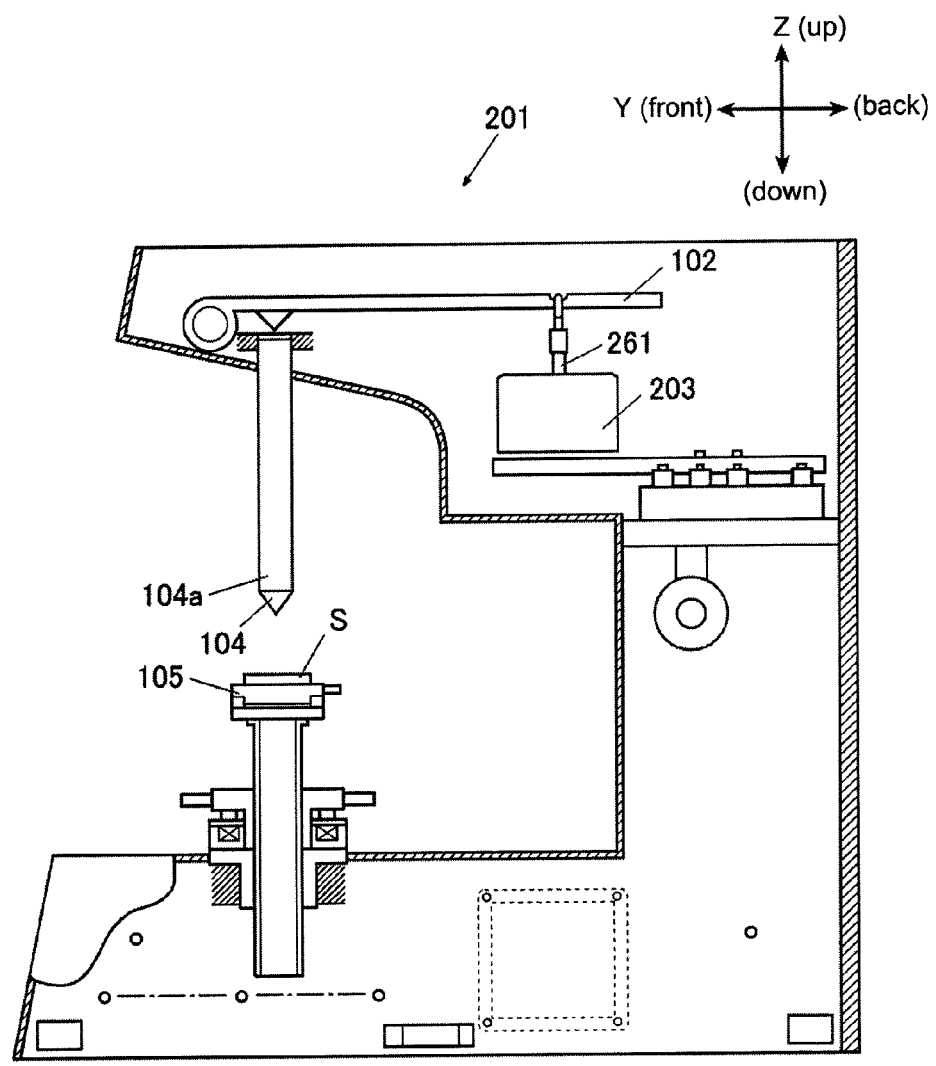
FIG. 11 is a right lateral view illustrating an overall configuration of a conventional hardness tester.
Figure 12:
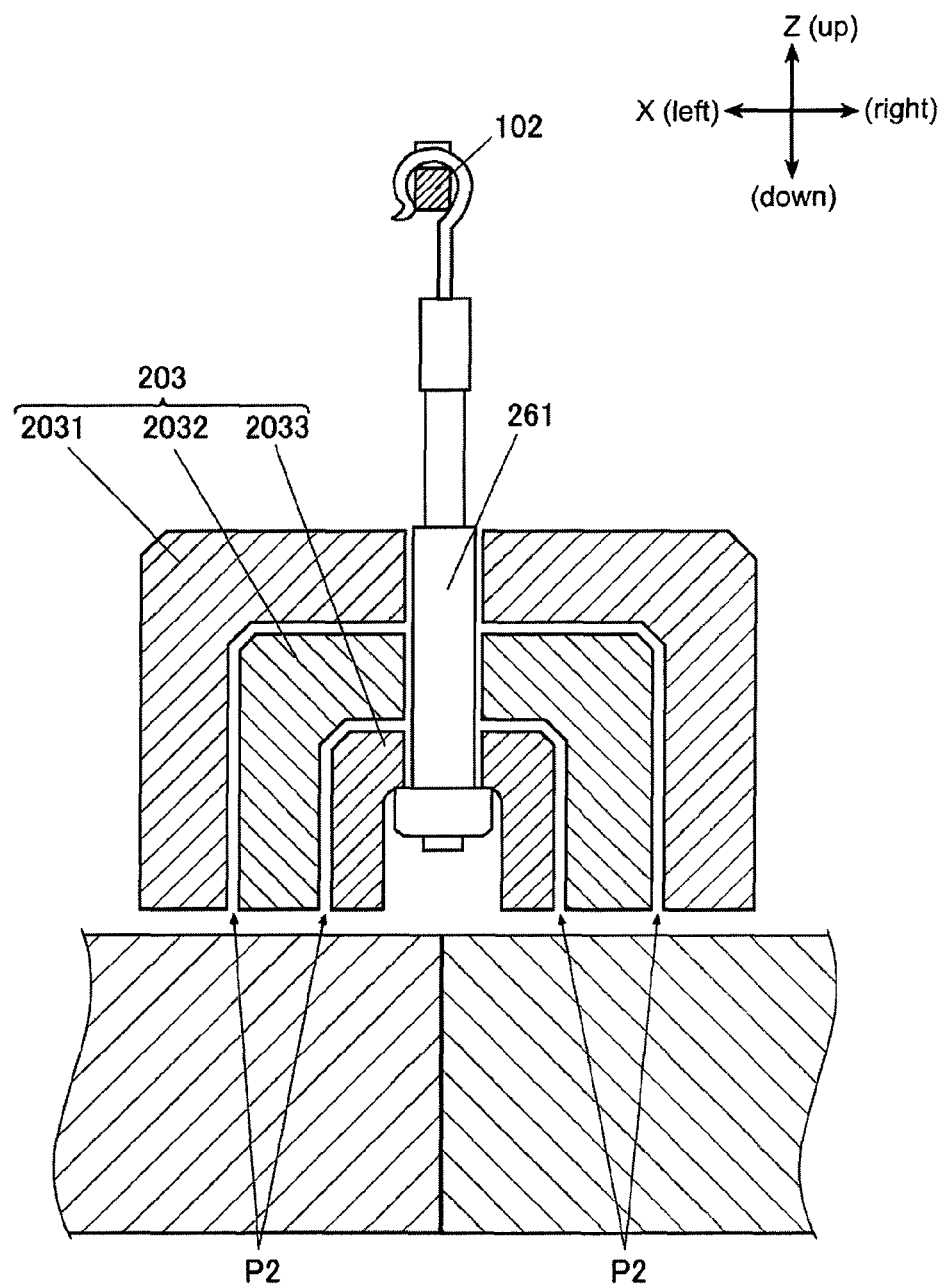
FIG. 12 is a cross-sectional view illustrating a configuration of a weight of the hardness tester of FIG. 11.

An example shown in FIGS. 9(A) to 9(C) differs from the embodiment in the structure of the test force switching mechanism 6. In order to simplify the description, identical reference numerals are used for structures similar to those in the embodiment and a detailed description thereof is omitted. Moreover, FIGS. 9(A) to 9(C) are treated as illustrating the weight 3 in a two-dot-dashed line. Specifically, in the example shown in FIGS. 9(A) to 9(C), a test force switching member 8 as a test force switcher is positioned so as to be capable of supporting a bottom end of the plurality of weights 31, 32, 33, and 34. In addition, the test force switching member 8 has a portion of a substantially rectangular shaped plate-shaped member cut away to form a notch 81 and form substantially a "V" shape, as seen in a plan view. The test force switching member 8 is configured to be capable of advance and retreat in a direction (horizontal direction) in which an open end 81a of the notch 81 is formed. The notch 81 is formed in substantially a recessed shape and is formed so as to increase in width toward an open end.

In an initial state illustrated in FIG. 9(A), the weights 31, 32, 33, and 34 are all resting on top of the test force switching member 8. Therefore, no load is acting on the weight engagement portion 22. Thus, the initial state is a state in which there is no load in the down direction acting on the load lever 2. For example, as shown in FIG. 9(B), when the test force switching member 8 is displaced to a position where the weights 31 and 32 are resting thereon, a load corresponding to the weights 33 and 34 is applied to the weight engagement portion 22. Accordingly, in the example shown in FIG. 9(B), a load in the down direction corresponding to the weights 33 and 34 is applied to the load lever 2. Moreover, although omitted from the drawings, when the position of the test force switching member 8 is adjusted to a position where only the weight 31 is resting thereon, a load in the down direction corresponding to the weights 32, 33, and 34 is applied to the load lever 2, and when adjusted to a position where the weights 31, 32, and 33 are resting thereon, a load in the down direction corresponding to the weight 34 is applied to the load lever 2. Also, as shown in FIG. 9(C), for example, when the test force switching member 8 is displaced to a position where none of the weights 31, 32, 33, and 34 are resting thereon, a load corresponding to all of the weights 31, 32, 33, and 34 is applied to the weight engagement portion 22. Thus, in the example shown in FIG. 9(C), a load in the down direction corresponding to all of the weights 31, 32, 33, and 34 is applied to the load lever 2. As noted above, the user adjusts the position of the test force switching member 8. Thus, a number of the weights 3 resting on top of the test force switching member 8 can be adjusted to select the load applied to the load lever 2. Specifically, the test force switching member 8 is advanced and withdrawn in the direction in which the open end 81a of the notch 81 is formed. Thus, it is possible to switch between which of the plurality of weights 31, 32, 33, and 34 is to be supported.

As noted above, according to the hardness tester 1 according to the alternate example 2, the test force switching member 8 includes the notch 81 positioned so as to be capable of supporting the bottom ends of the plurality of weights 31, 32, 33, and 34 and is formed so as to widen toward the open end. In addition, the test force switching member 8 is configured to be capable of advancing and retreating in the direction in which the open end 81a of the notch 81 is formed. By advancing and retreating the test force switching member 8 in the direction in which the open end 81a of the notch 81 is formed, it is possible to switch between which of the plurality of weights 31, 32, 33, and 34 is to be supported. Therefore, switching the test force with a single member can be achieved, and costs can be further reduced.

Additional Alternate Examples

In addition, in the above-described embodiment, the cam member 61 is rotated by controlling a driver such as a motor. However, the present invention is not limited to this. For example, calibration marks indicating the rotation angle of the cam member 61 may be provided and the cam member 61 may be rotated manually.

In addition, in the above-described embodiment, the test force switching mechanism 6 is provided such that the left-right-direction width H of the cam member 61 changes according to the rotation angle of the cam member 61. However, the present invention is not limited to this. For example, the test force switching mechanism 6 may be positioned such that a width of the cam member 61 in the front-back direction changes according to the rotation angle of the cam member 61. In addition, in the above-described embodiment, the cam member 61 formed in the shape of an "S" was described to exemplify the shape of the cam member 61. However, the present invention is not limited to this. Any shape may be used so long as the horizontal-direction width of the shape changes according to the rotation angle. For example, the shape may be an elliptical shape. In addition, in the above-described embodiment, by utilizing the cam member 61, switching of the test force by rotating a maximum of 90° can be achieved. However, the present invention is not limited to this, and switching of the test force by rotating 90° or more can be achieved by altering the shape of a cam member as appropriate.

In addition, an exemplary description is given of a case where the number of weights 3 is four in the above-described embodiment and the number of weights 7 is three in the alternate example 1. However, the present invention is not limited to this. Regarding the number of weights, a configuration of any number may be used so long as there is a plurality of weights because the configuration must be capable of switching between test forces. Also, in the embodiment and alternate example 1 described above, the weights 31, 32, 33, and 34 and the weights 71, 72, and 73 are stacked on top of each other in the vertical direction in order of lightness. However, the present invention is not limited to this. The weight of each of the weights 31, 32, 33, and 34 and the weights 71, 72, and 73 may be set as desired. For example, the weights 31, 32, 33, and 34 and the weights 71, 72, and 73 may be stacked on top of each other in order of heaviness, and the weights 31, 32, 33, and 34 and the weights 71, 72, and 73 may each have the same weight.

In addition, within a scope not deviating from the substance of the present invention, appropriate modifications may also be made to detailed structures and operations of each component configuring the hardness tester 1.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for measuring hardness of a sample by forming an indentation in a surface of a sample by applying a predetermined test force with an indenter, then measuring dimensions of the indentation, the hardness tester comprising:
   a plurality of weights stacked on top of each other in a vertical direction, the plurality of weights configured to apply the predetermined test force to the sample through the indenter and comprising:
      hollow portions running through a horizontal-direction center in the vertical direction; and
      accommodation portions formed so as to be capable of accommodating the weight located directly below, wherein:
         an exterior surface of the weights is provided with an outside tapered portion,
         an interior surface of the accommodation portion is provided with an inside tapered portion engaging with the outside tapered portion of the accommodated weight to regulate horizontal-direction displacement of the weight;
   a transmission configured to transmit to the indenter, as the test force, a force of gravity acting on the plurality of weights, the transmission comprising:
      a shaft running through the hollow portions, wherein a predetermined gap is present between the hollow portions and the shaft; and
      a weight engagement portion provided at a bottom end of the shaft and capable of being accommodated by the accommodation portion of the bottom-most weight to engage the weight, the weight engagement portion comprising a tapered portion configured to engage the inside tapered portion of the bottom-most weight to regulate the horizontal-direction displacement of the bottom-most weight; and
   a test force switch configured to switch a magnitude of the test force by switching between the weights applying the test force,
   wherein the test force switch comprises:
      a cam positioned below the plurality of weights and configured for rotation concentric with the plurality of weights, and formed such that a horizontal-direction width changes according to a rotation angle; and
      a weight support configured to support the weights and formed by a pair of members positioned so as to be mutually point-symmetrical in the horizontal direction with the cam therebetween, and a first end being rotatable around a vertical axis, wherein the weight support is configured to be continuously biased such that a second end closes toward the cam, and a distance between the second ends changes due to rotating the first ends, caused by rotation of the cam, such that the switching between which of the plurality of weights is to be supported can be performed.

2. The hardness tester according to claim 1, wherein the inside tapered portion of the bottom-most weight contacts an entire surface of the tapered portion of the weight engagement portion that is accommodated within the bottom-most weight.

3. A hardness tester for measuring hardness of a sample by forming an indentation in a surface of a sample by applying a predetermined test force with an indenter, then measuring dimensions of the indentation, the hardness tester comprising:
   a plurality of weights stacked on top of each other in a vertical direction, wherein the plurality of weights have a truncated cone shape when the plurality of weights is stacked on top of each other, and the plurality of weights configured to apply the predetermined test force to the sample through the indenter and comprising:
      hollow portions running through a horizontal-direction center in the vertical direction; and
      accommodation portions formed so as to be capable of accommodating the weight located directly below, wherein:
         an exterior surface of the weights is provided with an outside tapered portion,
         an interior surface of the accommodation portion is provided with an inside tapered portion engaging with the outside tapered portion of the accommodated weight to regulate horizontal-direction displacement of the weight;
   a transmission configured to transmit to the indenter, as the test force, a force of gravity acting on the plurality of weights, the transmission comprising:
      a shaft running through the hollow portions, wherein a predetermined gap is present between the hollow portions and the shaft; and
      a weight engagement portion provided at a bottom end of the shaft and capable of being accommodated by the accommodation portion of the bottom-most weight to engage the weight, the weight engagement portion comprising a tapered portion configured to engage the inside tapered portion of the bottom-most weight to regulate the horizontal-direction displacement of the bottom-most weight; and a test force switch configured to switch a magnitude of the test force by switching between the weights applying the test force, wherein the test force switch comprises:

a cam positioned below the plurality of weights and configured for rotation concentric with the plurality of weights, and formed such that a horizontal-direction width changes according to a rotation angle; and a weight support configured to support the weights and formed by a pair of members positioned so as to be mutually point-symmetrical in the horizontal direction with the cam therebetween, and a first end being rotatable around a vertical axis, wherein the weight support is configured to be continuously biased such that a second end closes toward the cam, and a distance between the second ends changes due to rotating the first ends, caused by rotation of the cam, such that the switching between which of the plurality of weights is to be supported can be performed.

4. A hardness tester for measuring hardness of a sample by forming an indentation in a surface of a sample by applying a predetermined test force with an indenter, then measuring dimensions of the indentation, the hardness tester comprising:

a plurality of weights stacked on top of each other in a vertical direction, the plurality of weights configured to apply the predetermined test force to the sample through the indenter and comprising:

hollow portions running through a horizontal-direction center in the vertical direction; and accommodation portions formed so as to be capable of accommodating the weight located directly below, wherein:

an exterior surface of the weights is provided with an outside tapered portion, an interior surface of the accommodation portion is provided with an inside tapered portion engaging with the outside tapered portion of the accommodated weight to regulate horizontal-direction displacement of the weight;

a transmission configured to transmit to the indenter, as the test force, a force of gravity acting on the plurality of weights, the transmission comprising:

a shaft running through the hollow portions, wherein a predetermined gap is present between the hollow portions and the shaft; and a weight engagement portion provided at a bottom end of the shaft and capable of being accommodated by the accommodation portion of the bottom-most weight to engage the weight, the weight engagement portion comprising a tapered portion configured to engage the inside tapered portion of the bottom-most weight to regulate the horizontal-direction displacement of the bottom-most weight; and a test force switch configured to switch a magnitude of the test force by switching between the weights applying the test force, wherein the test force switch comprises a notch configured to support bottom ends of the plurality of weights, the notch widening toward an open end, the test force switch further configured to advance and retreat in a direction in which the open end of the notch is formed such that switching between which of the plurality of weights is to be supported is performed by advancing and retreating the test force switcher in the direction in which the open end of the notch is formed.

5. A hardness tester for measuring hardness of a sample by forming an indentation in a surface of a sample by applying a predetermined test force with an indenter, then measuring dimensions of the indentation, the hardness tester comprising:

a plurality of weights stacked on top of each other in a vertical direction, wherein the plurality of weights have a truncated cone shape when the plurality of weights is stacked on top of each other, and the plurality of weights configured to apply the predetermined test force to the sample through the indenter and comprising:

hollow portions running through a horizontal-direction center in the vertical direction; and accommodation portions formed so as to be capable of accommodating the weight located directly below, wherein:

an exterior surface of the weights is provided with an outside tapered portion, an interior surface of the accommodation portion is provided with an inside tapered portion engaging with the outside tapered portion of the accommodated weight to regulate horizontal-direction displacement of the weight;

a transmission configured to transmit to the indenter, as the test force, a force of gravity acting on the plurality of weights, the transmission comprising:

a shaft running through the hollow portions, wherein a predetermined gap is present between the hollow portions and the shaft; and a weight engagement portion provided at a bottom end of the shaft and capable of being accommodated by the accommodation portion of the bottom-most weight to engage the weight, the weight engagement portion comprising a tapered portion configured to engage the inside tapered portion of the bottom-most weight to regulate the horizontal-direction displacement of the bottom-most weight; and a test force switch configured to switch a magnitude of the test force by switching between the weights applying the test force, wherein the test force switch comprises a notch configured to support bottom ends of the plurality of weights, the notch widening toward an open end, the test force switch further configured to advance and retreat in a direction in which the open end of the notch is formed such that switching between which of the plurality of weights is to be supported is performed by advancing and retreating the test force switcher in the direction in which the open end of the notch is formed.

\* \* \* \* \*